(12) United States Patent
Hursey

(10) Patent No.: US 8,252,344 B2
(45) Date of Patent: *Aug. 28, 2012

(54) PARTIALLY HYDRATED HEMOSTATIC AGENT

(75) Inventor: Francis X. Hursey, West Hartford, CT (US)

(73) Assignee: Z-Medica Corporation, Wallingford, CT (US)

( * ) Notice: Subject to any disclaimer, the term of this patent is extended or adjusted under 35 U.S.C. 154(b) by 1235 days.

This patent is subject to a terminal disclaimer.

(21) Appl. No.: 10/939,869

(22) Filed: Sep. 13, 2004

(65) Prior Publication Data

US 2005/0058721 A1    Mar. 17, 2005

Related U.S. Application Data

(60) Provisional application No. 60/502,571, filed on Sep. 12, 2003.

(51) Int. Cl.
*A61L 15/16* (2006.01)
*A61L 15/08* (2006.01)
*A61L 15/00* (2006.01)
*A61L 15/18* (2006.01)
*A61L 15/42* (2006.01)
*A61F 13/00* (2006.01)
*A61F 13/15* (2006.01)
*A61K 9/14* (2006.01)
*B01J 29/04* (2006.01)

(52) U.S. Cl. ........ 424/684; 424/682; 424/600; 424/618; 424/445; 424/489; 602/41; 602/42; 602/48; 502/60; 502/80; 502/400

(58) Field of Classification Search .......................... None
See application file for complete search history.

(56) References Cited

U.S. PATENT DOCUMENTS

| | | | |
|---|---|---|---|
| 2,688,586 A | 9/1954 | Eberl et al. | |
| 2,969,145 A | 1/1961 | Hannuer, Jr. | |
| 3,122,140 A | 2/1964 | Crowe et al. | |
| 3,181,231 A * | 5/1965 | Breck | 75/229 |
| 3,189,227 A | 6/1965 | Hobbs et al. | |
| 3,366,578 A * | 1/1968 | Michalko | 502/8 |
| 3,538,508 A | 11/1970 | Young | |
| 3,550,593 A | 12/1970 | Kaufman | |
| 3,723,352 A | 3/1973 | Warne et al. | |
| 3,979,335 A * | 9/1976 | Golovko et al. | 502/68 |
| 4,373,519 A | 2/1983 | Errede et al. | |
| 4,374,044 A | 2/1983 | Schaefer et al. | |
| 4,379,143 A * | 4/1983 | Sherry et al. | 424/684 |
| 4,435,512 A | 3/1984 | Ito et al. | |
| 4,460,642 A | 7/1984 | Errede et al. | |
| 4,514,510 A * | 4/1985 | Alexander | 501/148 |
| 4,524,064 A | 6/1985 | Nambu | |
| 4,525,410 A | 6/1985 | Hagiwara et al. | |
| 4,569,343 A | 2/1986 | Kimura et al. | |
| 4,626,550 A * | 12/1986 | Hertzenberg | 514/770 |
| 4,631,845 A | 12/1986 | Samuel et al. | |
| 4,651,725 A | 3/1987 | Kifune et al. | |
| 4,748,978 A | 6/1988 | Kamp | |
| 4,822,349 A * | 4/1989 | Hursey et al. | 424/445 |
| 4,828,081 A | 5/1989 | Nordstrom et al. | |
| 4,911,898 A | 3/1990 | Hagiwara et al. | |
| 4,938,958 A | 7/1990 | Niira et al. | |
| 4,956,350 A | 9/1990 | Mosbey | |
| 5,140,949 A * | 8/1992 | Chu et al. | 119/174 |
| 5,146,932 A | 9/1992 | McCabe | |
| 5,474,545 A | 12/1995 | Chikazawa | |
| 5,486,195 A | 1/1996 | Myers et al. | |
| 5,538,500 A | 7/1996 | Peterson | |
| 5,556,699 A | 9/1996 | Niira et al. | |
| 5,578,022 A | 11/1996 | Scherson et al. | |
| 5,597,581 A | 1/1997 | Kaessmann et al. | |
| 5,599,578 A | 2/1997 | Butland | |
| D386,002 S | 11/1997 | Hinkle | |
| 5,696,101 A | 12/1997 | Wu et al. | |
| 5,716,337 A | 2/1998 | McCabe et al. | |
| 5,725,551 A | 3/1998 | Myers et al. | |
| 5,728,451 A | 3/1998 | Langley et al. | |
| 5,766,715 A | 6/1998 | Garconnet | |
| 5,788,682 A | 8/1998 | Maget | |
| 5,801,116 A | 9/1998 | Cottrell et al. | |
| 5,826,543 A | 10/1998 | Raymond et al. | |
| 5,855,570 A | 1/1999 | Scherson et al. | |
| 5,916,511 A | 6/1999 | Kotani et al. | |
| 5,941,897 A | 8/1999 | Myers | |
| 5,964,239 A | 10/1999 | Loux et al. | |
| 5,964,349 A | 10/1999 | Odagiri | |
| 5,981,052 A | 11/1999 | Sugiyama | |
| 5,993,964 A | 11/1999 | Nakajima | |
| 6,037,280 A | 3/2000 | Edwards et al. | |
| 6,060,461 A | 5/2000 | Drake | |

(Continued)

FOREIGN PATENT DOCUMENTS

CA    1223208    6/1987
CN    1970090 A    5/2007

(Continued)

OTHER PUBLICATIONS

The Merck Index ;1989, pp. 1596-1597, abstract 10021.*

(Continued)

*Primary Examiner* — Kevin S Orwig
(74) *Attorney, Agent, or Firm* — Knobbe Martens Olson & Bear, LLP

(57) ABSTRACT

A composition for promoting the formation of clots in blood comprises a zeolite and a binder. The zeolite is adjusted to have a specific moisture content. Processes by which the moisture content is adjusted include drying, re-hydrating, and combinations of drying and re-hydrating. A method of forming the composition comprises the steps of providing a zeolite and adjusting the moisture content such that upon application of the composition to a wound, a heat of hydration is reduced and heat transferred to the wound is reduced. A method of clotting blood flowing from a wound comprises the steps of applying the zeolite to the wound and maintaining the zeolite in contact with the wound for a predetermined amount of time, the zeolite having an adjusted moisture content and being capable of producing a controllable exothermic effect on the wound.

9 Claims, No Drawings

U.S. PATENT DOCUMENTS

| | | | |
|---|---|---|---|
| 6,086,970 A | 7/2000 | Ren | |
| 6,123,925 A | 9/2000 | Barry et al. | |
| 6,159,232 A | 12/2000 | Nowakowski | |
| 6,187,347 B1 * | 2/2001 | Patterson et al. | 424/646 |
| 6,203,512 B1 | 3/2001 | Farris et al. | |
| 6,372,333 B1 | 4/2002 | Sugiyama et al. | |
| 6,428,800 B2 | 8/2002 | Greenspan et al. | |
| 6,450,537 B2 | 9/2002 | Norris | |
| 6,475,470 B1 | 11/2002 | Kayane et al. | |
| 6,481,134 B1 | 11/2002 | Aledo | |
| 6,486,285 B2 | 11/2002 | Fujita | |
| 6,495,367 B1 | 12/2002 | Isogawa et al. | |
| 6,523,778 B2 | 2/2003 | Key et al. | |
| 6,573,419 B2 | 6/2003 | Naimer | |
| 6,590,337 B1 | 7/2003 | Nishikawa et al. | |
| 6,622,856 B2 | 9/2003 | Gallo et al. | |
| 6,630,140 B1 | 10/2003 | Grunstein | |
| 6,685,227 B2 | 2/2004 | Merry et al. | |
| 6,700,032 B1 | 3/2004 | Gray | |
| 6,701,649 B1 | 3/2004 | Brosi | |
| 6,745,720 B2 | 6/2004 | Rasner et al. | |
| 6,998,510 B2 | 2/2006 | Buckman et al. | |
| 7,125,821 B2 | 10/2006 | Xu et al. | |
| 7,371,403 B2 | 5/2008 | McCarthy et al. | |
| 7,429,252 B2 | 9/2008 | Sarangapani | |
| 7,595,429 B2 | 9/2009 | Hursey | |
| 7,604,819 B2 | 10/2009 | Huey et al. | |
| 7,825,133 B2 | 11/2010 | Yi | |
| 7,858,123 B2 | 12/2010 | Stucky | |
| 7,968,114 B2 | 6/2011 | Huey et al. | |
| 8,063,264 B2 | 11/2011 | Spearman et al. | |
| 8,114,433 B2 | 2/2012 | Huey et al. | |
| 2002/0077653 A1 | 6/2002 | Hudson et al. | |
| 2002/0197302 A1 | 12/2002 | Cochrum et al. | |
| 2003/0133990 A1 | 7/2003 | Hursey et al. | |
| 2003/0175333 A1 | 9/2003 | Shefer et al. | |
| 2003/0176828 A1 | 9/2003 | Buckman et al. | |
| 2003/0199922 A1 | 10/2003 | Buckman | |
| 2003/0208150 A1 | 11/2003 | Bruder et al. | |
| 2003/0212357 A1 | 11/2003 | Pace | |
| 2004/0005350 A1 | 1/2004 | Looney et al. | |
| 2004/0038893 A1 | 2/2004 | Ladner et al. | |
| 2004/0166172 A1 | 8/2004 | Rosati et al. | |
| 2004/0169033 A1 | 9/2004 | Kuibira et al. | |
| 2004/0243043 A1 | 12/2004 | McCarthy et al. | |
| 2004/0249899 A1 | 12/2004 | Shiigi | |
| 2005/0023956 A1 | 2/2005 | Kwak et al. | |
| 2005/0058721 A1 | 3/2005 | Hursey | |
| 2005/0070693 A1 | 3/2005 | Hansen et al. | |
| 2005/0074505 A1 | 4/2005 | Hursey | |
| 2005/0107826 A1 | 5/2005 | Zhu et al. | |
| 2005/0118230 A1 | 6/2005 | Hill et al. | |
| 2005/0119112 A1 | 6/2005 | Pfenninger et al. | |
| 2005/0137815 A1 | 6/2005 | Campbell et al. | |
| 2005/0143689 A1 | 6/2005 | Ramsey, III | |
| 2005/0246009 A1 | 11/2005 | Toner et al. | |
| 2005/0248270 A1 | 11/2005 | Ghosh et al. | |
| 2006/0034935 A1 | 2/2006 | Pronovost et al. | |
| 2006/0078628 A1 | 4/2006 | Koman et al. | |
| 2006/0116635 A1 | 6/2006 | Van Heugten | |
| 2006/0121101 A1 | 6/2006 | Ladizinsky | |
| 2006/0141018 A1 | 6/2006 | Cochrum et al. | |
| 2006/0141060 A1 | 6/2006 | Hursey et al. | |
| 2006/0159733 A1 | 7/2006 | Pendharkar et al. | |
| 2006/0172000 A1 | 8/2006 | Cullen et al. | |
| 2006/0178609 A1 | 8/2006 | Horn et al. | |
| 2006/0193905 A1 | 8/2006 | Ehringer et al. | |
| 2006/0211965 A1 | 9/2006 | Horn et al. | |
| 2006/0211971 A1 | 9/2006 | Horn et al. | |
| 2006/0271094 A1 | 11/2006 | Hudson et al. | |
| 2006/0282046 A1 | 12/2006 | Horn et al. | |
| 2007/0016152 A1 | 1/2007 | Karpowicz et al. | |
| 2007/0031515 A1 | 2/2007 | Stucky et al. | |
| 2007/0065491 A1 | 3/2007 | Huey et al. | |
| 2007/0104768 A1 | 5/2007 | Huey et al. | |
| 2007/0104792 A1 | 5/2007 | Jenkins | |
| 2007/0134293 A1 | 6/2007 | Huey et al. | |
| 2007/0142783 A1 | 6/2007 | Huey et al. | |
| 2007/0154509 A1 | 7/2007 | Wilcher et al. | |
| 2007/0154510 A1 | 7/2007 | Wilcher et al. | |
| 2007/0154564 A1 | 7/2007 | Stucky et al. | |
| 2007/0160638 A1 | 7/2007 | Mentkow et al. | |
| 2007/0160653 A1 | 7/2007 | Fischer et al. | |
| 2007/0167971 A1 | 7/2007 | Huey et al. | |
| 2007/0251849 A1 | 11/2007 | Lo et al. | |
| 2007/0275073 A1 | 11/2007 | Huey et al. | |
| 2007/0276308 A1 | 11/2007 | Huey et al. | |
| 2007/0276345 A1 | 11/2007 | Huey et al. | |
| 2007/0281011 A1 | 12/2007 | Jenkins et al. | |
| 2008/0027365 A1 | 1/2008 | Huey | |
| 2008/0085300 A1 | 4/2008 | Huey et al. | |
| 2008/0097271 A1 | 4/2008 | Lo et al. | |
| 2008/0125686 A1 | 5/2008 | Lo | |
| 2008/0146984 A1 | 6/2008 | Campbell et al. | |
| 2008/0199539 A1 | 8/2008 | Baker et al. | |
| 2008/0206134 A1 | 8/2008 | Lo et al. | |
| 2008/0254146 A1 | 10/2008 | Huey et al. | |
| 2008/0254147 A1 | 10/2008 | Huey et al. | |
| 2008/0269658 A1 | 10/2008 | Vinton et al. | |
| 2008/0299226 A1 | 12/2008 | Mentkow et al. | |
| 2008/0317831 A1 | 12/2008 | Lo | |
| 2008/0319476 A1 | 12/2008 | Ward et al. | |
| 2009/0008261 A1 | 1/2009 | Kotzeva et al. | |
| 2009/0043268 A1 | 2/2009 | Eddy et al. | |
| 2009/0047366 A1 | 2/2009 | Bedard et al. | |
| 2009/0053288 A1 | 2/2009 | Eskridge, Jr. et al. | |
| 2009/0074880 A1 | 3/2009 | Ladizinsky | |
| 2009/0076475 A1 | 3/2009 | Ross et al. | |
| 2009/0112170 A1 | 4/2009 | Wells et al. | |
| 2009/0162406 A1 | 6/2009 | Basadonna et al. | |
| 2009/0186013 A1 | 7/2009 | Stucky | |
| 2009/0186071 A1 | 7/2009 | Huey et al. | |
| 2009/0232902 A1 | 9/2009 | Liu et al. | |
| 2009/0299253 A1 | 12/2009 | Hursey | |
| 2010/0035045 A1 | 2/2010 | McAmish | |
| 2010/0121244 A1 | 5/2010 | Horn et al. | |
| 2010/0209531 A2 | 8/2010 | Stucky et al. | |
| 2010/0228174 A1 | 9/2010 | Huey | |
| 2010/0233248 A1 | 9/2010 | Huey et al. | |
| 2011/0015565 A1 | 1/2011 | Hursey | |
| 2011/0268784 A1 | 11/2011 | Huey | |
| 2012/0004636 A1 | 1/2012 | Lo | |

FOREIGN PATENT DOCUMENTS

| | | |
|---|---|---|
| CN | 101104080 | 1/2008 |
| CN | 1114984 | 3/2008 |
| CN | 101541274 | 9/2009 |
| CN | 101687056 | 3/2010 |
| EP | 0 107 051 | 9/1983 |
| EP | 0 353 710 | 2/1990 |
| EP | 0826822 A2 | 3/1998 |
| EP | 0 888 783 A1 | 7/1999 |
| EP | 1159972 A2 | 5/2001 |
| EP | 1 663 090 | 6/2006 |
| EP | 1690553 A1 | 8/2006 |
| EP | 1714642 | 10/2006 |
| EP | 1810697 A2 | 7/2007 |
| EP | 1 679 087 | 1/2010 |
| EP | 2 142 220 | 1/2010 |
| EP | 2 292 196 | 3/2011 |
| GB | 2 259 858 | 3/1993 |
| GB | 2314842 | 1/1998 |
| GB | 2 462 228 | 2/2010 |
| HK | 1135892 | 6/2010 |
| IN | 241410 | 7/2010 |
| JP | 61145120 | 7/1986 |
| JP | 01-096558 | 10/1987 |
| JP | 2777279 B2 | 7/1998 |
| JP | 11-332909 A1 | 7/1999 |
| JP | 2004123651 | 7/2006 |
| TR | 2011 00164 T4 | 9/2004 |
| WO | WO 95/05445 * | 2/1995 |
| WO | WO 95/12371 | 5/1995 |
| WO | WO 96/40285 | 12/1996 |

| | | |
|---|---|---|
| WO | WO 99/13918 | 3/1999 |
| WO | WO 00/30694 | 6/2000 |
| WO | WO 00/66086 | 11/2000 |
| WO | 0182896 A1 | 11/2001 |
| WO | WO 01/97826 | 12/2001 |
| WO | WO 02/30479 | 4/2002 |
| WO | WO 02/30479 A1 | 4/2002 |
| WO | WO 02/060367 A1 | 8/2002 |
| WO | WO 02/074325 A1 | 9/2002 |
| WO | WO 03/074566 | 9/2003 |
| WO | WO 2005/012493 | 2/2005 |
| WO | WO 2005/027808 A1 | 3/2005 |
| WO | WO 2005/030279 | 4/2005 |
| WO | WO 2005/087280 | 9/2005 |
| WO | WO 2005/123170 | 12/2005 |
| WO | WO 2006/012218 A1 | 2/2006 |
| WO | WO 2006/086557 | 8/2006 |
| WO | WO 2006/088912 A2 | 8/2006 |
| WO | WO 2006/102008 | 9/2006 |
| WO | WO 2006/110393 | 10/2006 |
| WO | WO 2007/120342 A2 | 10/2007 |
| WO | WO 2008/036225 A2 | 3/2008 |
| WO | WO 2008/054566 | 5/2008 |
| WO | WO 2008/109160 | 9/2008 |
| WO | WO 2008/127497 | 10/2008 |
| WO | WO 2008/128149 | 10/2008 |
| WO | WO 2008/136806 | 11/2008 |
| WO | WO 2008/157536 | 12/2008 |
| WO | WO 2009/032884 | 3/2009 |
| WO | WO 2009/126917 | 10/2009 |

OTHER PUBLICATIONS

Supplemental European Search Report, Jan. 29, 2008.
Co-pending U.S. Appl. No. 10/939,687, filed Sep. 13, 2004.
Co-pending U.S. Appl. No. 11/023,869, filed Dec. 27, 2004.
Co-pending U.S. Appl. No. 11/082,716, filed Mar. 6, 2005.
Co-pending U.S. Appl. No. 11/303,607, filed Dec. 16, 2005.
Co-pending U.S. Appl. No. 11/404,126, filed Apr. 13, 2006.
Co-pending U.S. Appl. No. 11/584,079, filed Oct. 20, 2006.
Co-pending U.S. Appl. No. 11/586,968, filed Oct. 25, 2006.
Co-pending U.S. Appl. No. 11/606,617, filed Nov. 29, 2006.
Co-pending U.S. Appl. No. 11/634,531, filed Dec. 6, 2006.
Co-pending U.S. Appl. No. 11/654,409, filed Jan. 17, 2007.
Co-pending U.S. Appl. No. 11/710,106, filed Feb. 22, 2007.
Co-pending U.S. Appl. No. 12/101,336, filed Apr. 11, 2008.
Co-pending U.S. Appl. No. 12/101,346, filed Apr. 11, 2008.
Co-pending U.S. Appl. No. 12/140,356, filed Jun. 17, 2008.
Co-pending U.S. Appl. No. 12/204,129, filed Sep. 4, 2008.
Office Action for U.S. Appl. No. 11/398,161, dated Apr. 30, 2008.
PCT Search Report for PCT/US2004/29808, dated Feb. 24, 2005.
Search Report for EP 05020602, dated Jul. 6, 2006.
PCT Search Report for PCT/US2005/046700, dated Jul. 6, 2006.
International Search Report for Application PCT/US2006/012487, dated Sep. 12, 2006.
Search report for EP 06126082, dated May 11, 2007.
Search report for EP 06123557, dated Feb. 29, 2008.
International Search Report for Application No. PCT/US2008/075191, dated Nov. 17, 2008.
Hursey, et al., Bandage Using Molecular Sieves, Apr. 18, 2002, International Application Published Under the PCT, WO 02/30479 A1.
Alam, et al., Comparative Analysis of Hemostatic Agents in a Swine Model of Lethal Groin Injury, Jun. 2003, The Journal of Trauma Injury, Infection, and Critical Care, vol. 54, No. 6, pp. 1077-1082.
M. Gielen, Solid State Organometallic Chemistry: Methods and Applications Physical Organometallic Chemistry, 1999, New York John Wiley & Sons, Ltd. (UK), V. 2, p. 156.
Le Van Mao, Raymond et al. "Mesoporous Aluminosilicates prepared from Zeolites by Treatment with Ammonium Fluorosilicate." J. Mater. Chem. 1993. pp. 679-683, vol. 3, No. 6.
Dyer, A. et al. "Diffusion in heteroionic zeolites: Part 1. Diffusion of water in heteroionics natrolites." Microporous and Mesoporous Materials. 1998, pp. 27-38, vol. 21.

Wright, J.K, et al., "Thermal Injury Resulting from Application of a Granular Mineral Hemostatic Agent." The Journal of TRAUMA Injury, Infection, and Critical Care. 2004, pp. 224-230, vol. 57, No. 2.
Top, Ayben et al. "Silver, zinc, and copper exchange in a Na-clinoptilolite and resulting effect on antibacterial activity." Applied Clay Science. 2004, pp. 13-19, vol. 27.
Co-pending U.S. Appl. No. 11/054,918, filed Feb. 9, 2005.
Co-pending U.S. Appl. No. 11/590,427, filed Oct. 30, 2006.
Co-pending U.S. Appl. No. 11/592,477, filed Nov. 2, 2006.
Co-pending U.S. Appl. No. 11/633,687, filed Dec. 4, 2006.
Co-pending U.S. Appl. No. 11/634,673, filed Dec. 5, 2006.
Co-pending U.S. Appl. No. 11/715,057, filed Mar. 6, 2007.
Donald Voet & Judith Voet, "Molecular Physiology", Biochemistry, p. 1087-1096, vol. 64, 1990, John Wiley & Sons.
European Search Report for Application No. 05445078 dated Jun. 27, 2006.
IMA-EU, Kaolin, Oct. 2006, p. 1-2.
International Search Report for Application No. PCT/US2004/029812, dated Jun. 14, 2005.
International Search Report for Application No. PCT/US2006/004594, dated Nov. 3, 2006.
International Search Report for Application No. PCT/US2007/016509, dated Feb. 8, 2008.
Alam, et al., Application of a Zeolite Hemostatic Agent Achieves 100% Survival in a Lethal Model of Complex Groin Injury in Swine, May 2004, The Journal of Trauma Injury, Infection, and Critical Care, vol. 56, pp. 974-983.
Aldrich—Handbook of Fine Chemicals and Laboratory Equipment, 2000-2001, pp. 1177-1178.
Analgesics and Anti-inflammatory agents 2004, retrieved from the internet on May 26, 2010, URL: http://web.archive.org/web/20040904151322/http://faculty.weber.edu/ewalker/Medicinal_Chemistry/topics/Analgesia_antiinflam/Analgesics_anti-inflamitory.htm.
Army halts use of new first aid item to study more, Seattle PI, Dec. 24, 2008.
Army halts use of WoundStat, http://stripes.com, Apr. 23, 2009.
Army pulls anti clotting agent after Fort Sam study finds threat, MySanAntonio Military, Dec. 24, 2008.
Baker, Sarah E. et al., Controlling Bioprocesses with Inorganic Surfaces: Layered Clay Hemostatic Agents, Department of Chemistry and Biochemistry, University of California, Santa Barbara, American Chemical Association 2007, 19, pp. 4390-4392 (3 pages total).
Bethesda, MD, TraumaCure, Life-saving News for Battlefield Soldiers & Wounded Civilians FDA Clears Product to Stop Severe Bleeding, Sep. 10, 2007.
Butenas—Mechanism of factor VIIa-dependent coagulation in hemophilia blood, Hemostasis, Thrombosis, and Vascular Biology, BLOOD, Feb. 1, 2002—vol. 99, No. 3.
CA Office Action re Application No. 2,590,595, filed Dec. 22, 2005, Office Action dated Apr. 17, 2009.
CA Office Action re Application No. 2,597,243 Feb. 8, 2006, Office Action dated Apr. 12, 2010.
Carraway, et al., Comparison of a new mineral based hemostatic agent to a commercially available granular zeolite agent for hemostasis in a swine model of lethal extremity arterial hemorrhage, Resuscitation vol. 78, Issue 2.
Clay makers (raw materials) retrieved from the internet on Mar. 15, 2010, URL: http://web.archive.org/web/20020609175053/http://www.claymaker.com/ceramic_central/info/raw_clays.htm (year 2002, pp. 104).
CN First Office Action re Application No. 200580039691.5, filed Dec. 22, 2005, First Office Action dated Jul. 24, 2009.
CN First Office Action re Application No. 200680008795.4, filed Feb. 8, 2006, First Office Action dated Jan. 8, 2010.
CN Second Office Action re Application No. 200680008795.4, filed Feb. 8, 2006, Second Office Action dated Jun. 29, 2010.
EPO Exam Report dated Dec. 2, 2008 re EP App. No. 06123557.8.
EPO Exam Report dated Jul. 18, 2007 re EP App. No. 05445078.8.
EPO Exam Report dated Sep. 22, 2009 re EP App. No. 06123557.8.
EPO Exam Report for EP 05020602, dated Oct. 16, 2007.
EPO Exam Report for EP 05020602, dated Sep. 15, 2006.
EPO Examination Report dated Mar. 30, 2010 re EP 08726591.4.

EPO Examination Report dated Mar. 30, 2010 re EP App. No. 07836179.7.
EPO Examination Report dated Sep. 4, 2009 re EP App. No. 07836179.7.
EPO Examination Report for Application No. EP04783867 dated Nov. 27, 2008.
EPO Search Report and Opinion, re EP 1 797 850, dated May 11, 2007.
EPO Supplemental Search Report re EP 1 663 090, dated Jun. 22, 2010.
EPO Supplementary Partial European Search Report for Application No. EP04783867 dated Jun. 22, 2010.
Fruijtier-Polloth, "The safety of synthetic zeolites used in detergents", Arch Toxicol (2009) 83:23-25.
Galan, et al.: "Technical properties of compound kaolin sample from griva (Macedonia, Greece)", Applied Clay Science 1996 10:477-490.
Gibbar-Clements, et al.: "The Challenge of Warfarin Therapy", JSTOR: The American Journal of Nursing,vol. 100, No. 3 (Mar. 2000), pp. 38-40.
Griffin, John H., Role of surface in surface-dependent activation of Hageman factor (blood coagulation Factor XII), Proc. Natl. Acad. Sci. USA, vol. 75, No. 4, Apr. 1978, pp. 1998-2002 (5 pages total).
HemCon Medical Technologies Inc. 501(k) Summary, GhitoGauze, Mar. 20, 2009.
IN First Office Action re Application No. 3474/CHENP/2007, filed Feb. 8, 2006, First Office Action dated Sep. 8, 2009.
International Preliminary Report and Written Opinion for Application No. PCT/US2007/023265, dated Sep. 29, 2009.
International Preliminary Report and Written Opinion for PCT/US2004/029809, dated Mar. 13, 2006.
International Preliminary Report and Written Opinion re PCT/US2006/004594, dated Aug. 14, 2007.
International Preliminary Report and Written Opinion Report for Application No. PCT/US2008/060177, dated Oct. 13, 2009.
International Report on Patentability and Written Opinion for Application No. PCT/US2008/003082, dated Sep. 29, 2009.
International Search Report for Application No. PCT/US2006/012487, dated Sep. 12, 2006.
International Search Report for Application No. PCT/US2007/023265, dated Sep. 17, 2009.
International Search Report for Application No. PCT/US2008/003082, dated Sep. 24, 2009.
International Search Report for Application No. PCT/US2008/060177, dated Jun. 22, 2009.
James, "Silver Copper Zeolite Guinea Pig Sensitization Study—Beuhler Method", Data Evaluation Report dated Oct. 3, 1989.
JP Office Action re Application No. 2006-301871, filed Nov. 7, 2006, Office Action dated Jul. 6, 2010.
Kheirabadi, Army Assessment of New Hemostatic Products Suitable for Treating Combat Wounds, US Army Institute of Surgical Research, Aug. 11, 2008.
Kheirabadi, et al., Session IV-B, Paper 28, 8:20 a.m., Comparison of New Hemostatic Dressings with Currently Deployed Hemcon Bandage in a Model of Extremity Arterial Hemorrhage in Swine.
Kheirabadi, et al., The Journal of TRAUMA Injury, Infection, and Critical Care, Comparison of New Hemostatic Granules/Powders with Currently Deployed Hemostatic Products in a Lethal model of Extremity Arterial Hemorrhage in Swine, Feb. 2009, pp. 316-328.
Kheirabadi, Final Report, Title: Assessment of Efficacy of New Hemostatic Agents in a Model of Extremity Arterial Hemorrhage in Swine, U.S. Army Institute of Surgical Research, Ft. Sam Houston, TX 78234, Mar. 4, 2008.
Macrina, VCU's Research Enterprise, Structure and Resources, Oct. 23, 2008.
Margolis, J., The Kaolin Clotting Time: A Rapid One-Stage Method for Diagnosis of Coagulation Defects, J. Clin. Pathol 1958, 11, pp. 406-409 (5 pages total).
Okada, et al.: "Preparation of zeolite-coated cordierite honeycombs prepared by an in situ crystallization method", Science and Technology of Advanced Materials 2004 5:479-484.

O'Reilly et al.: "Studies on Coumarin Anticoagulant Drugs—Initiaion of Warfarin Therapy Without a Loading Dose", Circulation by the American Heart Association, http://circ.ahajournals.org, 1968, 38, 169-177.
Ore-Medix, Traumastat Hemostatic Bandage, Aug. 7, 2008.
Permanent suspension of Woundstat use, https://email.z-medica.com.
Reprinted related contents of US Alaract regarding QuikClot CombatGauze.
Sadler et al.: "Biochemstry and Genetics of Van Willebrand Factor", Annual Review of Biochemistry; 1998. 67:395-424.
Scott Sackinger's Medical Devices Professional Summary dated Mar. 2009.
Sinter. (2004). In The New Penguin Dictionary of Science. London: Penguin. Retrieved May 7, 2009, from http://www.credoreference.com/entry/7463549/.
Comparative Testing of Hemostatic Dressings in a Severe Groin Hemorrhage, Trauma & Resuscitative Medicine Department, NMRC.
Tactical Combat Casualty Care Guidelines, Feb. 2009.
TraumaCure, Innovative Wound Care Products for Wound Care Solutions.
Vitrify—(2001). In Chambers 21s5t Century Dictionary. London. Chambers Harrap. Retrieved May 7, 2009, from http://www.credoreference.com/entry/1236485/.
Ward, et al., The Journal of TRAUMA Injury, Infection, and Critical Care, Comparison of a New Hemostatic Agent to Current Combat Hemostatic Agents in a Swine Model of Lethal Extremity Arterial Hemorrhage, Aug. 2007, pp. 276-284.
WoundStat found to be potentially hazardous, http://armytimes.com.
Z-Medica Corporation 510(k) Summary, QuikClot eX, Oct. 4, 2007.
U.S. Appl. No. 10/939,687, filed Sep. 13, 2004 including prosecution history, including but not limited to Non-Final Rejection dated Oct. 16, 2006, Final Rejection dated May 24, 2007, Non-Final Rejection dated Sep. 6, 2007, Final Rejection dated Nov. 28, 2007 and Examiner's Answer to Appeal Brief.
U.S. Appl. No. 11/023,869, filed Dec. 27, 2004 including prosecution history, including but not limited to Requirement for Restriction/Election dated Mar. 31, 2008, Non-Final Rejection dated May 12, 2008 and Non-Final Rejection dated Dec. 11, 2008.
U.S. Appl. No. 11/054,918, filed Feb. 9, 2005 including prosecution history, including but not limited to Non-Final Office Rejection dated Mar. 18, 2008, Final Rejection dated Sep. 16, 2008 and Non-Final Rejection dated Mar. 9, 2009.
U.S. Appl. No. 11/082,716, filed Mar. 16, 2005 including prosecution history, including but not limited to Non-Final Rejection dated Oct. 9, 2008.
U.S. Appl. No. 11/303,607 filed Dec. 16, 2005 including prosecution history, including but not limited to Requirement for Restriction/Election dated Feb. 21, 2008, Non-Final Rejection dated Apr. 29, 2008 and Non-Final Rejection dated Sep. 8, 2008.
U.S. Appl. No. 11/404,126 filed Apr. 13, 2006 including prosecution history, including but not limited to Requirement for Restriction/Election dated Sep. 16, 2008 and Non-Final Rejection dated Dec. 3, 2008.
U.S. Appl. No. 11/544,238, filed Oct. 6, 2006 including prosecution history, including but not limited to Requirement for Restriction/Election dated Dec. 11, 2008; Non-Final Office Action dated May 29, 2009.
U.S. Appl. No. 11/584,079, filed Oct. 20, 2006 including prosecution history, including but not limited to Non-Final Rejection dated Apr. 6, 2009.
U.S. Appl. No. 11/590,427, filed Oct. 30, 2006 including prosecution history, including but not limited to Non-Final Rejection dated Aug. 19, 2008 and Final Rejection dated May 26, 2009.
U.S. Appl. No. 11/592,477 filed Nov. 2, 2006 including prosecution history, including but not limited to Non-Final Rejection dated May 28, 2008 and Final Rejection dated Dec. 22, 2008.
U.S. Appl. No. 11/633,687, filed Dec. 4, 2006 including prosecution history, including but not limited to Requirement for Restriction/Election dated Jun. 25, 2008; Non-Final Rejection dated Sep. 4, 2998 and Final Office Action dated Jun. 1, 2009.

U.S. Appl. No. 11/634,673, filed Dec. 5, 2006 including prosecution history, including but not limited to Requirement for Restriction/Election dated Apr. 9, 2008, Non-Final Rejection dated May 12, 2008, Final Rejection dated Nov. 14, 2008 and Non-Final Rejection dated May 21, 2009.
U.S. Appl. No. 11/715,057, filed Mar. 6, 2007 including prosecution history, including but not limited to Non-Final Rejection dated Aug. 20, 2008 and Final Rejection dated Apr. 2, 2009.
U.S. Appl. No. 12/417,802, filed Apr. 3, 2009 including prosecution history.
US Offce Action re U.S. Appl. No. 11/584,079, filed Oct. 20, 2006, Office Action dated Apr. 6, 2009.
US Offce Action re U.S. Appl. No. 12/417,802, filed Apr. 3, 2009, Office Action dated Jun. 11, 2010.
US Office Action re U.S. Appl. No. 11/023,869, filed Dec. 27, 2004, Office Action dated Dec. 11, 2008.
US Office Action re U.S. Appl. No. 11/023,869, filed Dec. 27, 2004, Office Action dated Jan. 26, 2010.
US Office Action re U.S. Appl. No. 11/023,869, filed Dec. 27, 2004, Office Action dated May 12, 2008.
US Office Action re U.S. Appl. No. 11/054,918, filed Feb. 9, 2005, Office Action dated Mar. 18, 2008.
US Office Action re U.S. Appl. No. 11/082,716, filed Mar. 16, 2005, Office Action dated Oct. 9, 208.
US Office Action re U.S. Appl. No. 11/303,607, filed Dec. 16, 2005, Office Action dated Apr. 29, 2008.
US Office Action re U.S. Appl. No. 11/303,607, filed Dec. 16, 2005, Office Action dated Sep. 8, 2008.
US Office Action re U.S. Appl. No. 11/404,126, filed Apr. 13, 2006, Office Action dated Dec. 21, 2009.
US Office Action re U.S. Appl. No. 11/404,126, filed Apr. 13, 2006, Office Action dated Dec. 3, 2008.
US Office Action re U.S. Appl. No. 11/544,238, filed Oct. 6, 2006, Office Action dated Jun. 25, 2010.
US Office Action re U.S. Appl. No. 11/544,238, filed Oct. 6, 2006, Office Action dated May 29, 2009.
US Office Action re U.S. Appl. No. 11/586,968, filed Oct. 25, 2006, Office Action dated Feb. 19, 2010.
US Office Action re U.S. Appl. No. 11/586,968, filed Oct. 25, 2006, Office Action dated Jun. 3, 2010.
US Office Action re U.S. Appl. No. 11/590,427, filed Oct. 30, 2006, Office Action dated Aug. 19, 2008.
US Office Action re U.S. Appl. No. 11/590,427, filed Oct. 30, 2006, Office Action dated Jun. 7, 2010.
US Office Action re U.S. Appl. No. 11/590,427, filed Oct. 30, 2006, Office Action dated May 26, 2009.
US Office Action re U.S. Appl. No. 11/592,477, filed Nov. 2, 2006, Office Action dated Dec. 22, 2008.
US Office Action re U.S. Appl. No. 11/592,477, filed Nov. 2, 2006, Office Action dated Jun. 18, 2009.
US Office Action re U.S. Appl. No. 11/592,477, filed Nov. 2, 2006, Office Action dated May 28, 2008.
US Office Action re U.S. Appl. No. 11/606,617, filed Nov. 29, 2006, Office Action dated Jun. 12, 2009.
US Office Action re U.S. Appl. No. 11/633,687, filed Dec. 14, 2006, Office Action dated Jun. 1, 2009.
US Office Action re U.S. Appl. No. 11/633,687, filed Dec. 14, 2006, Office Action dated Sep. 4, 2008.
US Office Action re U.S. Appl. No. 11/634,531, filed Dec. 6, 2006, Office Action dated Feb. 4, 2009.
US Office Action re U.S. Appl. No. 11/634,531, filed Dec. 6, 2006, Office Action dated Mar. 29, 2010.
US Office Action re U.S. Appl. No. 11/634,531, filed Dec. 6, 2006, Office Action dated Sep. 4, 2009.
US Office Action re U.S. Appl. No. 11/634,673, filed Dec. 5, 2006, Final Office Action dated Mar. 25, 2010.
US Office Action re U.S. Appl. No. 11/634,673, filed Dec. 5, 2006, Office Action dated May 12, 2008.
US Office Action re U.S. Appl. No. 11/634,673, filed Dec. 5, 2006, Office Action dated May 21, 2009.
US Office Action re U.S. Appl. No. 11/634,673, filed Dec. 5, 2006, Office Action dated Nov. 14, 2008.

US Office Action re U.S. Appl. No. 11/654,409, filed Jan. 17, 2007, Office Action dated Mar. 30, 2010.
US Office Action re U.S. Appl. No. 12/101,336, filed Apr. 11, 2008, Office Action dated Mar. 22, 2010.
US Office Action re U.S. Appl. No. 12/101,346, filed Apr. 11, 2008, Office Action dated Mar. 19, 2010.
CA Office Action re Application No. 2,665,108, filed Jul. 20, 2007, Office Action dated Aug. 24, 2010.
CA Office Action re Application No. 2,677,606 filed Mar. 6, 2008, Office Action dated Jul. 27, 2010.
IN Office Action, Indian Application No. 2844/DELNP/2007, dated Aug. 13, 2010.
International Preliminary Report and Written Opinion re PCT/US2008/006517, dated Nov. 24, 2009.
US Office Action re U.S. Appl. No. 11/404,126, filed Apr. 13, 2006, Notice of Abandonment dated Oct. 8, 2010.
US Office Action re U.S. Appl. No. 11/634,531, filed Dec. 6, 2006, Final Office Action dated Oct. 5, 2010.
US Office Action re U.S. Appl. No. 11/710,106, filed Feb. 22, 2007, Office Action dated Oct. 1, 2010.
US Office Action re U.S. Appl. No. 12/101,336, filed Apr. 11, 2008, Notice of Abandonment dated Oct. 7, 2010.
US Office Action re U.S. Appl. No. 12/101,346, filed Apr. 11, 2008, Office Action dated Sep. 15, 2010.
US Office Action re U.S. Appl. No. 12/140,356, filed Jun. 17, 2008, Office Action dated Sep. 28, 2010.
Co-pending U.S. Appl. No. 11/544,238, filed Oct. 6, 2006.
Basadonna, G., et al.: "A novel kaolin coated surgical gauze improves hemostasis both in vitro and in vivo", Journal of Surgical Research, vol. 144, No. 2, Feb. 2008, p. 440, XP002534658, abstract.
Japanese Office Action re Application No. JP 2009-534569, dated Nov. 15, 2010.
Kovzun, I. G., et al.: "Application of nanosize clay-mineral systems in the complex therapy for hemophilia "A" patients", Database HCAPLUS [online], XP002534657, retrieved from STN Database accession No. 2009:502758 abstract & Nanosistemi, Nanomateriali, Nanotekhnologii, vol. 6, No. 2, 2008.
PCT International Report on Patentability and Written Opinion re PCT/US2009/040256, dated Oct. 12, 2010.
PCT International Search Report re PCT/US2009/040256, dated Aug. 4, 2009.
US Office Action re U.S. Appl. No. 10/939,869, filed Sep. 13, 2004, Final Office Action dated Dec. 12, 2010.
US Office Action re U.S. Appl. No. 11/023,869, filed Dec. 27, 2004, Office Action dated Sep. 16, 2010.
US Office Action re U.S. Appl. No. 11/654,409, filed Jan. 17, 2007, Final Office Action dated Oct. 25, 2010.
US Office Action re U.S. Appl. No. 12/503,481, filed Jul. 15, 2009, Office Action Dated Dec. 27, 2010.
US Office Action re U.S. Appl. No. 12/555,876, filed Sep. 9, 2009, Office Action dated Dec. 28, 2010.
Griffin, John H., "Role of surface in surface-dependent activation of Hageman factor (blood Coagulation Factor XII)", Proc. Natl. Acad. Sci. USA, Apr. 1978, vol. 75, No. 4, pp. 1998-2002.
Margolis, J., "Initiation of Blood Coagulation by Glass and Related Surfaces", J. Physoil., 1957, vol. 137, pp. 95-109.
Wagner, Holly, "Topical Oxygen Helps Hard-To-Heal Wounds Heal Faster and Better," Jan. 28, 2003, obtained from http://researchnews.osu.edu/archive/oxvwound.htm.
Wright, J. Barry et al.: "Wound management in an era of increasing bacterial antibiotic resistance: A role for topical silver treatment", American Journal of Infection Control, vol. 26 (6), 1998, pp. 572-577.
U.S Appl. No. 10/939,869, filed Sep. 13, 2004, including its prosecution history, including, but not limited to, Final Office Action dated May 17, 2011 and Interview Summary dated Jul. 27, 2011.
U.S Appl. No. 12/140,356, filed Jun. 17, 2008, including its prosecution history, including, but not limited to, Final Office Action dated Mar. 21, 2011.
U.S Appl. No. 11/634,531, filed Dec. 6, 2006, including its prosecution history, including, but not limited to, Office Action dated Jun. 23, 2011.

U.S Appl. No. 12/204,129, filed Sep. 4, 2008, including its prosecution history, including, but not limited to, Office Action dated May 31, 2011.
U.S Appl. No. 12/417,802, filed Apr. 3, 2009, including its prosecution history, including, but not limited to, Office Action dated Jan. 25, 2011.
U.S Appl. No. 12/503,481, filed Jul. 15, 2009, including its prosecution history, including, but not limited to, Office Action dated Jul. 5, 2011.
U.S Appl. No. 12/555,876, filed Sep. 9, 2009, including its prosecution history, including, but not limited to, Office Action dated May 27, 2011.
U.S Appl. No. 12/581,782, filed Oct. 19, 2009, including its prosecution history, including, but not limited to, Office Action dated Mar. 16, 2011 and Response to Office Action dated Jul. 18, 2011.
U.S Appl. No. 11/590,427, filed Oct. 30, 2006, including its prosecution history, including, but not limited to, Notice of Allowance dated Apr. 5, 2011.
Angeloni, V., M.D.: "How to care for your wound.", Heartland Dermatology & Skin Cancer P. C., copyright 2001, V. Angeloni MD.
Griffin, J. H.: "Role of surface in surface-dependent activation of Hageman factor (blood coagulation Factor XII)", Proc. Natl. Acad. Sci. USA, vol. 75, No. 4, pp. 1998-2002, Apr. 1978 Medical Sciences.
Margolis, "Initiation of Blood Coagulation by Glass and Related Surfaces", J. Physiol. (1957) 137, 95-109.
PCT International Search Report re Application No. PCT/US2010/041741, dated Nov. 26, 2010.
U.S. Appl. No. 12/352,513, filed Jan. 12, 2009 including prosecution history.
U.S. Appl. No. 10/939,869, filed Sep. 13, 2004 including prosecution history, including but not limited to Non-Final Rejection dated Feb. 8, 2008, Non-Final Rejection dated Sep. 17, 2008, Final Rejection dated Apr. 17, 2009, Final Office Action dated Apr. 1, 2010, Final Office Action dated Dec. 12, 2010; Office Action dated May 17, 2011.
U.S. Appl. No. 11/023,869, filed Dec. 27, 2004 including prosecution history, including but not limited to Requirement for Restriction/Election dated Mar. 31, 2008, Non-Final Rejection dated May 12, 2008, Non-Final Rejection dated Dec. 11, 2008; Office Action dated Jan. 26, 2010; and Office Action dated Sep. 16, 2010.
U.S. Appl. No. 11/404,126, filed Apr. 13, 2006 including prosecution history, including but not limited to Requirement for Restriction/Election dated Sep. 16, 2008, Non-Final Rejection dated Dec. 3, 2008, Office Action dated Dec. 21, 2009 and Notice of Abandonment dated Oct. 8, 2010.
U.S. Appl. No. 11/544,238, filed Oct. 6, 2006 including prosecution history, including but not limited to Requirement for Restriction/Election dated Dec. 11, 2008; Non-Final Office Action dated May 29, 2009; and Office Action dated Jun. 25, 2010.
U.S. Appl. No. 11/586,968, filed Oct. 25, 2006 including prosecution history, including but not limited to Office Action dated Feb. 19, 2010 and Office Action dated Jun. 3, 2010.
U.S. Appl. No. 11/590,427, filed Oct. 30, 2006 including prosecution history, including but not limited to Non-Final Rejection dated Aug. 19, 2008 and Final Rejection dated May 26, 2009; Office Action dated Jun. 7, 2010 and Notice of Allowance dated Apr. 5, 2011.
U.S. Appl. No. 11/592,477, filed Nov. 2, 2006 including prosecution history, including but not limited to Non-Final Rejection dated May 28, 2008 and Final Rejection dated Dec. 22, 2008 and Office Action dated Jun. 18, 2009.
U.S. Appl. No. 11/606,617, filed Nov. 29, 2006, including prosecution history,including but not limited to Office Action dated Jun. 12, 2009.
U.S. Appl. No. 11/634,531, filed Dec. 6, 2006, including prosecution history, including but not limited to Office Action dated Feb. 4, 2009; Office Action dated Sep. 4, 2009, Office Action dated Mar. 29, 2010; Final Office Action dated Oct. 5, 2010; Office Action date Jun. 23, 2011.
U.S. Appl. No. 11/634,673, filed Dec. 5, 2006, including prosecution history, including but not limited to Requirement for Restriction/Election dated Apr. 9, 2008, Non-Final Rejection dated May 12, 2008, Final Rejection dated Nov. 14, 2008 and Non-Final Rejection dated May 21, 2009 and Final Office Action dated Mar. 25, 2010.

U.S. Appl. No. 11/654,409, filed Jan. 17, 2007, including prosecution history, including but not limited to Office Action dated Mar. 3, 2010 and Final Office Action dated Oct. 25, 2010.
U.S. Appl. No. 11/710,106, filed Feb. 22, 2007, including prosecution history, including but not limited to Office Action dated Oct. 1, 2010.
U.S. Appl. No. 12/101,336, filed Apr. 11, 2008, including prosecution history, including but not limited to Office Action dated Mar. 22, 2010 and Notice of Abandonment dated Oct. 7, 2010.
U.S. Appl. No. 12/101,346, filed Apr. 11, 2008, including prosecution history, including but not limited to Office Action dated Mar. 19, 2010 and Office Action dated Sep. 15, 2010.
U.S. Appl. No. 12/140,356, filed Jun. 17, 2008, including prosecution history, including but not limited to Final Office Action dated Sep. 28, 2010, and Office Action dated Mar. 21, 2011.
U.S. Appl. No. 12/204,129, filed Sep. 4, 2008, including prosecution history, including but not limited to Office Action dated May 31, 2011 and Nov. 17, 2011.
U.S. Appl. No. 12/417,802, filed Apr. 3, 2009 including prosecution history, including but not limited to Office Action dated Jan. 25, 2011 and US Office Action dated Jun. 11, 2010 and Office Action dated Jan. 25, 2011.
U.S. Appl. No. 12/503,481, filed Jul. 15, 2009, including prosecution history, including but not limited to Office Action dated Dec. 27, 2010 and Office dated Jul. 5, 2011.
U.S. Appl. No. 12/510,203, filed Jul. 27, 2009, including prosecution history, including but not limited to, Office Action dated Sep. 26, 2011.
U.S. Appl. No. 12/555,876, filed Sep. 9, 2009, including prosecution history, including but not limited to Office Action dated Dec. 28, 2010 and Office Action dated May 27, 2011.
U.S. Appl. No. 12/581,782, filed Oct. 19, 2009, including prosecution history, including but not limited to Office Action dated Mar. 16, 2011.
U.S. Appl. No. 13/175,380, filed Jul. 1, 2011, including prosecution history.
U.S. Appl. No. 60/668,022, filed Apr. 4, 2005.
U.S. Appl. No. 60/708,206, filed Aug. 15, 2005.
U.S. Appl. No. 60/902,738, filed Feb. 21, 2007.
U.S. Appl. No. 60/955,854, filed Aug. 14, 2007.
U.S. Appl. No. 10/939,869, filed Sep. 13, 2004, including prosecution history, including but not limited to Office Action date May 17, 2011.
CALOPLAST (Kaoline Poultice), South African Electronic Package Inserts, Information presented by Malahyde Information Systems, Copyright 1996-1998, printed from home.intekom.com/pharm/allied/caloplst.html#INDICATIONS, two pages.
Reprinted related contents of US Alaract regarding QuikClot CombatGauze, Sep. 2008.
Vlok, Marie E.: "Kaoline poultice", Manual of Nursing, vol. 1, Basic Nursing, revised ninth edition, p. 649. Copyright Juta & Co, Ltd., Lansdowne, South Africa, first published 1962.
Wound Stat, http://shadowspear.com/vb/showthread.php?t=16586 dated Dec. 22, 2008, last accessed Apr. 16, 2009.
WoundStat found to be potentially hazardous, Army News, news from Iraq . . . . , http://armytimes.com/news/2009/04/armLwoundstat_042009w/, posted Apr. 20, 2009, last accessed Apr. 20, 2009.
U.S. Appl. No. 12/510,203, filed Jul. 27, 2009, including prosecution history, including but not limited to, Office Action dated Sep. 26, 2011 and Feb. 24, 2012.
U.S. Appl. No. 12/611,830, filed Nov. 3, 2009, including prosecution history, including but not limited to Office Action dated Nov. 4, 2011 and Notice of Allowance dated Feb. 1, 2012.
U.S. Appl. No. 10/939,869, filed Sep. 13, 2004, including prosecution history, including prosecution history, including but not limited to Final Office Action dated May 17, 2011.
U.S. Appl. No. 12/140,356, filed Jun. 17, 2008, including prosecution history, including but not limited to Final Office Action dated Mar. 21, 2011.

U.S. Appl. No. 60/668,022, filed Apr. 4, 2005, including prosecution history.
U.S. Appl. No. 60/708,206, filed Aug. 15, 2005, including prosecution history.
U.S. Appl. No. 60/902,738, filed Feb. 21, 2007, including prosecution history.

U.S. Appl. No. 60/955,854, filed Aug. 14, 2007, including prosecution history.
U.S. Appl. No. 12/352,513, filed Jan. 12, 2009.

* cited by examiner

PARTIALLY HYDRATED HEMOSTATIC AGENT

CROSS REFERENCE TO RELATED APPLICATION

This application claims the benefit of U.S. Provisional Patent Application No. 60/502,571 filed Sep. 12, 2003, entitled "Blood Clotting Compositions and Wound Dressings," to Francis X. Hursey, the contents of which are incorporated herein by reference.

TECHNICAL FIELD

The present invention relates to blood clotting devices (also referred to as hemostatic agents) and methods of controlling bleeding and, more particularly, to blood clotting materials and compositions for use as bleeding control devices.

BACKGROUND OF THE INVENTION

Blood is a liquid tissue that includes red cells, white cells, corpuscles, and platelets dispersed in a liquid phase. The liquid phase is plasma, which includes acids, lipids, solubilized electrolytes, and proteins. The proteins are suspended in the liquid phase and can be separated out of the liquid phase by any of a variety of methods such as filtration, centrifugation, electrophoresis, and immunochemical techniques. One particular protein suspended in the liquid phase is fibrinogen. When bleeding occurs, the fibrinogen reacts with water and thrombin (an enzyme) to form fibrin, which is insoluble in blood and polymerizes to form clots.

In a wide variety of circumstances, animals, including humans, can be wounded. Often bleeding is associated with such wounds. In some instances, the wound and the bleeding are minor, and normal blood clotting functions in addition to the application of simple first aid are all that is required. Unfortunately, however, in other circumstances, substantial bleeding can occur. These situations usually require specialized equipment and materials as well as personnel trained to administer appropriate aid. If such aid is not readily available, excessive blood loss can occur. When bleeding is severe, sometimes the immediate availability of equipment and trained personnel is still insufficient to stanch the flow of blood in a timely manner.

Moreover, severe wounds can often be inflicted in very remote areas or in situations, such as on a battlefield, where adequate medical assistance is not immediately available. In these instances, it is important to stop bleeding, even in less severe wounds, long enough to allow the injured person or animal to receive medical attention.

In an effort to address the above-described problems, materials have been developed for controlling excessive bleeding in situations where conventional aid is unavailable or less than optimally effective. Although these materials have been shown to be somewhat successful, they are not effective enough for traumatic wounds and tend to be expensive. Furthermore, these materials are sometimes ineffective in all situations and can be difficult to apply as well as remove from a wound. Additionally, or alternatively, they can produce undesirable side effects.

Compositions for promoting the formation of clots in blood have also been developed. Such compositions generally comprise zeolites and binders. In a typical zeolite/binder composition, the water content is estimated to be about 1.54% or less. The water content is estimated by measuring the mass of material before and after heating at 550 degrees C. (Loss on Ignition (LOI) at 550 degrees C.). Higher temperatures are sometimes used for LOI calculations, but procedures that utilize these higher temperatures increase the loss of chemical compounds other than water.

Based on the foregoing, it is a general object of the present invention to provide a bleeding control device that overcomes or improves upon the prior art.

SUMMARY OF THE INVENTION

According to one aspect of the present invention, a composition for promoting the formation of clots in blood comprises a zeolite and a binder. In such a composition, the moisture content of the zeolite is adjusted by drying, re-hydrating, or a combination of drying and re-hydrating such that the zeolite has a specific moisture content. Alternatively, the composition may be fully saturated with water and subsequently dried to a specific water content. In the drying of the zeolite, the bound water is removed to allow the crystalline structure of the zeolite to remain intact. In the re-hydration of the zeolite, the most active adsorption sites are hydrated first and then less active sites are hydrated. As the zeolite's degree of hydration increases, the heat of hydration decreases. More specifically, when the composition is applied to the blood, water in the blood is adsorbed by the zeolite. Upon adsorption of this water, heat is generated. At higher levels of hydration (hydration of the zeolite prior to its application to blood), less heat is generated when the composition is applied to blood. Thus, when the composition is applied to blood directly at a wound site, the amount of heat transferred to the tissue surrounding the wound site is reduced.

According to another aspect of the present invention, a method of forming a blood-clotting composition comprises the steps of providing a zeolite in hydrated form and adjusting a moisture content of the zeolite to have a specific moisture content such that upon application of the composition to a wound, a heat of hydration is reduced and a heat transferred to the wound is reduced.

According to another aspect of the present invention, a method of clotting blood flowing from a wound comprises the steps of applying a zeolite to the wound and maintaining the zeolite in contact with the wound for a predetermined amount of time, the zeolite having an adjusted moisture content and being capable of producing a controllable exothermic effect on the wound.

One advantage of the present invention is that it is easily applied to an open wound. It can be readily removed from sterilized packaging and deposited directly at the points from which blood emanates to dress the wound.

Another advantage of the present invention is that the rate of water adsorption is dramatically reduced as the degree of hydration increases from about 0.1% to about 4%. After about 4%, the rate of adsorption is slower. Also, after about 4%, the rate of adsorption changes more slowly. In application of the composition to promote the clotting of blood, slower water adsorption is advantageous for two reasons. First, the humidity and temperature of the packaging environment has less of an affect, thereby allowing material to be exposed to the environment for a longer period of time without significantly changing the pre-hydration level. Second, the slower rate of water adsorption allows the heat of hydration to be dissipated over a longer period of time. Therefore, the composition is heated to a lower maximum temperature. Thus, less heat is transferred to the tissue of a wound without losing product efficacy (formation of clots in blood).

The present invention is able to effectively clot traumic bleeding of wounds better than other available methods for treating similar wounds. For example, in a lethal femoral swine model in which several blood clotting materials were evaluated, the material of the present invention was the only material proven to have a morbidity rate of 0% including a standard pressure dressing.

DETAILED DESCRIPTION OF THE PREFERRED EMBODIMENTS

Disclosed herein are compositions and methods directed to the clotting of blood and the forming of blood clotting compositions. The compositions generally include molecular sieves for minimizing or stopping bleeding by absorbing at least portions of the liquid phases of blood, thereby promoting clotting. The methods generally include the application of molecular sieves to bleeding wounds to provide dressings and removing components of the blood to facilitate the formation of clots.

In one embodiment of the present invention, a molecular sieve comprises a zeolite and a binder. As used herein, the term "zeolite" refers to a crystalline form of aluminosilicate that may include several ionic species including sodium and calcium moieties. The preferred molecular structure of the zeolite is referred to as an "A-type" crystal. As used herein, the term "A-type crystal" is intended to indicate a crystal having a cubic crystalline structure and round holes. The zeolite may be ion-exchanged to include a specific cation, for example, calcium, sodium, potassium, silver, or magnesium, or any combination of the foregoing. Suitable zeolites for use in the applications disclosed herein are also preferably nanoporous so as to provide increased surface areas. As used herein, the term "nanoporous" is intended to indicate an average pore diameter of about 3 angstroms to about 5 angstroms.

In another embodiment of the present invention, the zeolite comprises irregularly-shaped granular material that is prepared by grinding larger particles and then selecting material that will pass through a 16 mesh sieve screen but will not pass through a 40 mesh sieve screen. The resulting zeolite is a composition of irregular granules that range in size from 0.4 millimeters (mm) in diameter to 0.8 mm in diameter.

Zeolites for use in the disclosed applications may be naturally occurring or synthetically produced. Numerous varieties of naturally occurring zeolites are found as deposits in sedimentary environments as well as in other places. Naturally occurring zeolites that may be applicable to the compositions and methods described herein include, but are not limited to, analcite, chabazite, heulandite, natrolite, stilbite, and thomosonite. Synthetically produced zeolites that may also find use in the compositions and methods described herein are generally produced by processes in which rare earth oxides are substituted by silicates, alumina, or alumina in combination with alkali or alkaline earth metal oxides.

The binder is preferably clay-based and may further include fillers (e.g., aluminum sulfate) or thickening agents that facilitate the selective application of the zeolite in various forms (e.g., as a paste, gel, powder, or erodable solid member). Natural clays that may provide suitable bases include, but are not limited to, kaolin, kaolinite, bentonite, montmorillonite, combinations of the foregoing clays, and the like. Modified clays such as polyorganosilcate graft polymers may also provide suitable bases.

In the preparation of the zeolite for a blood clotting composition, the moisture content of the zeolite is adjusted by drying, re-hydrating, or a combination of drying and re-hydrating the zeolite such that the zeolite has a specific moisture content. A fully hydrated zeolite has a moisture content of about 20 weight percent (wt. %). Drying of the zeolite may be effected by the application of heat. Upon heating, adsorbed water bound in the crystalline structure is driven off without altering the structure itself or detracting from its integrity. The dried zeolite may then be re-hydrated. The efficacy provided by the molecular sieve material/zeolite is enhanced by rehydrating the molecular sieve material/zeolite to a hydration level ranging between 1% and 15%. In addition, it has been found that this hydration level more preferables between about 2% and 8%. The exothermia caused by the reaction of the molecular sieve material/zeolite with the blood flowing from an open wound can be reduced to a level which virtually eliminates any potential damage to the surrounding Upon drying or drying and re-hydrating, in another example, the zeolite contains about 1.55 wt. % to about 10 wt. % moisture, and preferably about 1.55 wt. % to about 4 wt. % moisture. Alternatively, the drying process can be stopped before the material is completely dehydrated. The final hydration of the material can be controlled by monitoring and controlling the temperature of zones of a drying apparatus in which the material is dried.

The hydrated zeolite material also generates less heat upon being fully-saturated with water in the application of the zeolite to the blood. In particular, the heat of hydration is inversely proportional to the moisture content. Therefore, a zeolite hydrated to a moisture content of 4 wt. % will generate measurably less heat than a zeolite that has been fully dehydrated to less than 0.1 wt. %. Both materials, however, will be fully-saturated with water upon application to a bleeding wound. Thus, when applied to a bleeding wound under conditions of actual use, the exothermic effects and heat transferred to the wound are reduced. Therefore, upon application of the composition of the present invention to a bleeding wound, less heat is transferred to the tissue of the wound.

As stated above, upon treating wounds with the present invention, the remaining blood, which includes cells, corpuscles, platelets, and plasma, is concentrated. The platelets aggregate and interact with collagen, phospholipids, and lipid-containing proteins in the plasma. The aggregation of the platelets provide nuclei upon which fibrin binds to form a clot. Cells from the blood subsequently combine with the clot to form a mass. When blood emanates from the wound, the formation of the mass from the clot causes the flow of blood to cease, thereby eliminating further loss of blood. The blood pressure will often noticeably increase upon application of the present invention due to cessation of blood loss.

EXAMPLE 1

Comparison of Supernatant Phase of Zeolite-Reacted Plasma with Serum

A molecular sieve containing partially re-hydrated zeolite was added to normal pooled plasma. Upon completion of the ensuing reaction, the plasma was separated into two phases, namely, a heavy phase and a supernatant phase. The heavy phase included the typical blood plasma components as well as the reacted zeolite. The supernatant phase was tested to determine the levels of PT, aPTT, and fibrinogen, where "PT" is prothrombin time and "aPTT" is activated partial thromboplastin time. As used herein, PT and aPPT are assays that provide time values that are compared to other samples or to a hemotological standard. The time values are used indirectly to suggest the levels of clotting factors present in pooled plasma. A control comprising serum was also tested to determine the levels of the same components. In a comparison of the supernatant phase to the control, it was noted that the PT, aPTT, and fibrinogen levels were comparable, thereby suggesting that factors indicative of the clotting of blood were depleted by the addition of the molecular sieve containing partially re-hydrated zeolite.

EXAMPLE 2

Determination of Exothermic Effect of Zeolite-Reacted Plasma

Varying amounts of a molecular sieve containing zeolite were added to 1 milliliter (ml) samples of normal pooled plasma. In the first sample, 200 milligram (mg) of the molecular sieve was added and reacted, and a temperature increase of 9 centigrade (C) degrees was observed. In the second sample, about 3.8 mg of the molecular sieve was added and reacted, and a temperature increase of less than 1 C. degree was observed.

Although this invention has been shown and described with respect to the detailed embodiments thereof, it will be understood by those of skill in the art that various changes may be made and equivalents may be substituted for elements thereof without departing from the scope of the invention. In addition, modifications may be made to adapt a particular situation or material to the teachings of the invention without departing from the essential scope thereof. Therefore, it is intended that the invention not be limited to the particular embodiments disclosed in the above detailed description, but that the invention will include all embodiments falling within the scope of the appended claims.

What is claimed is:

1. A composition for promoting clotting of blood, said composition comprising:
    a binder comprising a clay; and
    a partially hydrated zeolite disposed in said binder;
    wherein the composition is in a solid form;
    wherein said zeolite has a moisture content of from 10% to 15% water by weight;
    wherein said moisture content of the partially hydrated zeolite is configured to provide a substantially reduced heat of hydration upon application of said partially hydrated zeolite to a wound, as compared to a completely dried amount of said zeolite; and
    wherein the partially hydrated zeolite with said moisture content is configured to accelerate clotting of blood.

2. The composition of claim 1, wherein said zeolite comprises aluminosilicate A-type crystals.

3. The composition of claim 1, wherein said zeolite is ion-exchanged to include a cation selected from the group consisting of calcium, sodium, potassium, silver, magnesium, and combinations of any of the foregoing cations.

4. The composition of claim 1, wherein said zeolite is nanoporous.

5. The composition of claim 1, wherein said composition is of an irregularly shaped granular form having a size distribution determined by sieving ground material with 40 mesh and 16 mesh cut-off screens.

6. A method of forming a blood-clotting composition, said method comprising the steps of:
    providing a zeolite in a solid form; adjusting a moisture content of said zeolite to have a specific moisture content from 10% to 15% water by weight;
    such that upon application of said composition to a wound, a heat of hydration is reduced and heat transferred to said wound is reduced as compared to a completely dried amount of said zeolite.

7. The method of claim 6, wherein said adjusting said moisture content of said zeolite comprises incompletely drying said zeolite.

8. The method of claim 6, wherein said adjusting said moisture content of said zeolite comprises incompletely re-hydrating said zeolite.

9. A method of clotting blood flowing from a wound, said method comprising the steps of:
    applying a zeolite to said wound, said zeolite having an adjusted moisture content that is at least 10% water by weight and less than 15% water by weight, and said zeolite is capable of reducing the amount of heat generated by contact between the zeolite and the flowing blood as compared to a completely dried amount of said zeolite;
    wherein the zeolite is capable of accelerating clotting of blood; and
    wherein the zeolite is in a solid form;
    maintaining said zeolite in contact with said wound for an amount of time sufficient to substantially reduce the flow of blood.

* * * * *